US006985763B2

(12) United States Patent
Boas et al.

(10) Patent No.: US 6,985,763 B2
(45) Date of Patent: Jan. 10, 2006

(54) METHOD FOR MEASURING VENOUS OXYGEN SATURATION

(75) Inventors: David Boas, Newmarket, NH (US); Maria Angela Franceschini, Winchester, MA (US); Sergio Fantini, Winchester, MA (US)

(73) Assignee: Tufts University, Boston, MA (US)

( * ) Notice: Subject to any disclaimer, the term of this patent is extended or adjusted under 35 U.S.C. 154(b) by 126 days.

(21) Appl. No.: 10/466,447

(22) PCT Filed: Nov. 30, 2001

(86) PCT No.: PCT/US01/45093

§ 371 (c)(1),
(2), (4) Date: Feb. 20, 2004

(87) PCT Pub. No.: WO02/056760

PCT Pub. Date: Jul. 25, 2002

(65) Prior Publication Data

US 2004/0122300 A1    Jun. 24, 2004

Related U.S. Application Data

(60) Provisional application No. 60/263,011, filed on Jan. 19, 2001.

(51) Int. Cl.
*A61B 5/00*    (2006.01)

(52) U.S. Cl. .................................... 600/323

(58) Field of Classification Search ............... 600/310, 600/322, 323, 330, 336
See application file for complete search history.

(56) References Cited

U.S. PATENT DOCUMENTS

5,253,646 A    10/1993  Delpy et al.
5,413,098 A     5/1995  Benaron

OTHER PUBLICATIONS

Y. Mendelson, "Pulse Oximetry: Theory and Applications for Noninvasive Monitoring," Clin. Chem. 38, 1601-1607 (1992).

C. Nolte et al. "Characterization of the pulse signal over the human head by near infrared spectroscopy," Adv. Exp. Med. Biol. 454, 115-123 (1998).

V. Toronov et al. "Near-Infrared Study of Fluctuations in Cerebral Hemodynamics During Rest and Motor Stimulation: Spatial Mapping and Temporal Analysis," Med. Phys. 27, 801-815 (2000).

(Continued)

*Primary Examiner*—Eric F. Winakur
(74) *Attorney, Agent, or Firm*—Greer, Burns & Crain, LTD (57) ABSTRACT

A method for measuring venous oxygen saturation levels has steps of measuring optical absorption oscillation data at the respiratory frequency at a plurality of wavelengths (2). A reduced scattering coefficient and an absorption coefficient are determined for the tissue, with the result that an effective path length can be determined (6). Data processing is performed to calculate amplitudes for the absorption oscillation data that are translated into oxygenated and deoxygenated hemoglobin concentrations for the venous compartment (8). A method of the invention does not required mechanical ventilation devices or venous perturbation. Additional method steps may entail verifying that the measured absorption oscillation data results from the venous compartment.

27 Claims, 7 Drawing Sheets

OTHER PUBLICATIONS

M. Wolf et al. "Continuous noninvasive measurement of cerebral arterial and venous oxygen saturation at the bedside in mechanically ventilated neonates," Crit. Care Med. 9, 1579-1582 (1997).

S. Fantini et al. "Frequency-Domain Multichannel Optical Detector for non-Invasive Tissue Spectroscopy and Oximetry," Opt. Eng. 34, 32-42 (1995).

M. A. Franceschini et al. "Optical Study of the Skeletal Muscle During Exercise with a Second Generation Frequency-Domain Tissue Oximeter," in *Optical Tomography and Spectroscopy of Tissue: Thoery, Instrumentation, Model, and Human Studies II*, B. Chance and R. R. Alfano, Editors, Proc. SPIE 2979, 807-814 (1997).

M. A. Franceschini et al. "Non-Invasive Optical Method to Measure Tissue and Arterial Saturation: an Application to Absolute Pulse Oximetry of the Brain," Opt. Lett. 24, 829-831 (1999).

B. Chance et al. "Phase measurement of light absorption and scatter in human tissues," Rev. Sci. Instru. 689, 3457-3481 (1998).

A. Zourabian et al. "Trans-abdominal monitoring of fetal arterial blood oxygenation using pulse oximetry," Journal of Biomedical Optics 5, 391-405 (2000).

S. Fantini et al. "Quantitative Determination of the Absorption Spectra of Chromophores in Strongly Scattering Media: a Light-Emitting-Diode Based Technique," Appl. Opt. 33, 5204-5213 (1994).

E. Gratton et al. "Measurements of Scattering and Absorption Changes in Muscle and Brain," Phil. Trans. R. Soc. of Lond. B 352, 727-735 (1997).

FIG. 5(a): PROBE PLACED ON CALF

FIG. 5(b): VENOUS OCCLUSION APPLIED AT THIGH

FIG. 5

METHOD FOR MEASURING VENOUS OXYGEN SATURATION

PRIORITY CLAIM

This application claims priority of U.S. Ser. No. 60/263,011 filed Jan. 19, 2001.

STATEMENT OF GOVERNMENT INTEREST

This invention was made with United States government support through the National Institutes of Health, Grant No. MH62584. The government has certain rights in this invention.

The present invention is related to apparatuses and methods that utilize spectrometry to determine oxygen saturation levels of tissue. More particularly, the present invention is related to apparatuses and methods that utilize near infrared spectrometry to non-invasively determine oxygen saturation levels of venous compartments.

BACKGROUND ART

The use of spectrometry to measure tissue oxygen saturation levels in a non-invasive manner is known in a general sense. Indeed, efforts to exploit the oxygenation dependent light absorption properties of hemoglobin to determine the oxygen saturation of hemoglobin in vivo have been made for several decades. In the 1980's so-called "pulse oximeters" became commercially available, and have continued to develop. An important advantage of such instruments is their ability to provide continuous, safe, and effective monitoring of arterial oxygenation non-invasively at a patient's bedside.

Pulse oximeters operate on the known principle that oxygenated and deoxygenated hemoglobin show different absorption spectra. Deoxygenated hemoglobin absorbs more light in the red band (typically 650–750 nm), while oxygenated hemoglobin absorbs more light in the infrared band (typically 850–1000 nm). Pulse oximeters generally use one wavelength in the near infrared band and one in the red band to measure the oxygen saturation of arterial blood. Traditionally, pulse oximetery has faced problems associated with determining the scatter that occurs in tissue. Without such a determination, accurate measures of absorption are not possible. Typically this problem has been addressed by "calibrating" devices on a population of healthy subjects to empirically determine levels of scatter.

Recent advances in pulse oximetry have been made. For example, the introduction of time-resolved optical spectroscopy in conjunction with diffusion theory has lead to quantitative tissue spectroscopy, as described in U.S. Pat. No. 5,497,769 to Gratton et al. ("the '769 patent"), which is incorporated by reference herein. The '769 patent generally discloses an apparatus useful for measuring the hemoglobin saturation in tissue that is particularly sensitive to blood in the capillaries where oxygen is exchanged with the tissue. Thus the '769 patent generally teaches an apparatus useful for measuring tissue oxygen saturation to give an indication of tissue oxygen consumption, but does not measure time-varying hemoglobin compartment saturation.

More recently, U.S. Pat. No. 6,216,021 to Franceschini et al. discloses a spectrometry-based method for the real time, non-invasive, simultaneous measurement of tissue hemoglobin saturation and time varying arterial hemoglobin saturation. The '769 patent provides a solution to the tissue scatter problem. Generally, the light signal is measured at two locations to determine tissue optical properties. The optical properties determine the amount of scatter that occurs as light travels through tissue. To determine time varying hemoglobin compartment saturation, an amplitude of absorption oscillations at the frequency of arterial pulsation is quantitatively calculated at multiple wavelengths from the oscillations of the optical signal collected by the spectrometer using the determined tissue optical properties, with the result that an absolute value of the arterial hemoglobin saturation may then be determined. Determination and use of the tissue optical properties allows the method of the '021 patent to be used without prior calibration of a spectrometer on a population of healthy subjects.

The teachings of the prior art, however, have generally been ineffective in regards to measurement of venous compartment saturation levels. Experimental approaches have been proposed for such measurements. For instance, the use of spectrometry in combination with physical manipulation of a patient has been proposed. Physical manipulations associated with these methods include use of a venous occlusion on a limb, tilting a patient's head downward, use of a partial jugular vein occlusion, use of mechanical ventilation, and the like. Generally, these methods contemplate optically measuring the venous saturation by measuring the increase in oxygenated hemoglobin concentration and in the total hemoglobin concentration induced by the local increase in the venous blood volume. All of these proposed methods, however, have significant disadvantages associated with them. Required physical manipulation of the patient, for instance, can be cumbersome, painful, and at times impractical. Additionally, these methods may be limited to use on the limbs (e.g., venous occlusion methods).

Additional unresolved problems in the art relate to verifying the accuracy of venous compartment measurements. That is, the proposed methods of the prior art generally have a considerable level of uncertainty associated with them. This uncertainty results from the many difficulties faced in isolating the venous compartment contribution to optical tissue absorption measurements.

Unresolved needs in the art therefore exist.

DISCLOSURE OF THE INVENTION

The present invention is directed to methods and program products for non-invasively determining the venous oxygen saturation. Generally, these methods and program products are directed to optically measuring oscillations at the respiratory frequency of a subject and use a data processing step to determine an amplitude of the absorption oscillations. Using the oscillation amplitude data, a venous oxygenation saturation level may be determined. Methods of the invention do not require that the subject be ventilated with mechanical ventilation devices or the like, or that venous perturbations be used. It will be appreciated, however, that methods of the invention may be used under such circumstances.

Preferably, the optical measurements are performed at a plurality of wavelengths. Data processing may comprise calculating an amplitude at each of the plurality of wavelengths using particular processing steps. As examples, particular data processing may comprise performing a Fourier transformation, or applying a band pass filter in combination with a modeling algorithm. A method of the invention also may comprise steps for verifying the accuracy of venous saturation level measurement.

The present invention thereby resolves many otherwise unsolved problems in the art. For example, levels of venous oxygenation may be accurately measured without requiring mechanical ventilation or venous perturbation of a subject. Additionally, embodiments of the invention offer novel steps that solve otherwise unresolved problems in the art related to verifying that measured absorption result from the venous compartment.

BEST MODE OF CARRYING OUT THE INVENTION

Other features, objects and advantages of the invention will be apparent to those skilled in the art by reference to the detailed description in view of the drawings, of which.

DETAILED DESCRIPTION

The present invention is directed to methods and program products for determining venous oxygen saturation levels through optical measurements performed at the respiratory frequency. More particularly, the present invention is directed to methods and program products whereby the amplitude of optical absorption oscillations are determined at the respiratory frequency, with data processing then applied to convert the absorption data into oxygenated and deoxygenated hemoglobin levels.

Figure 1:
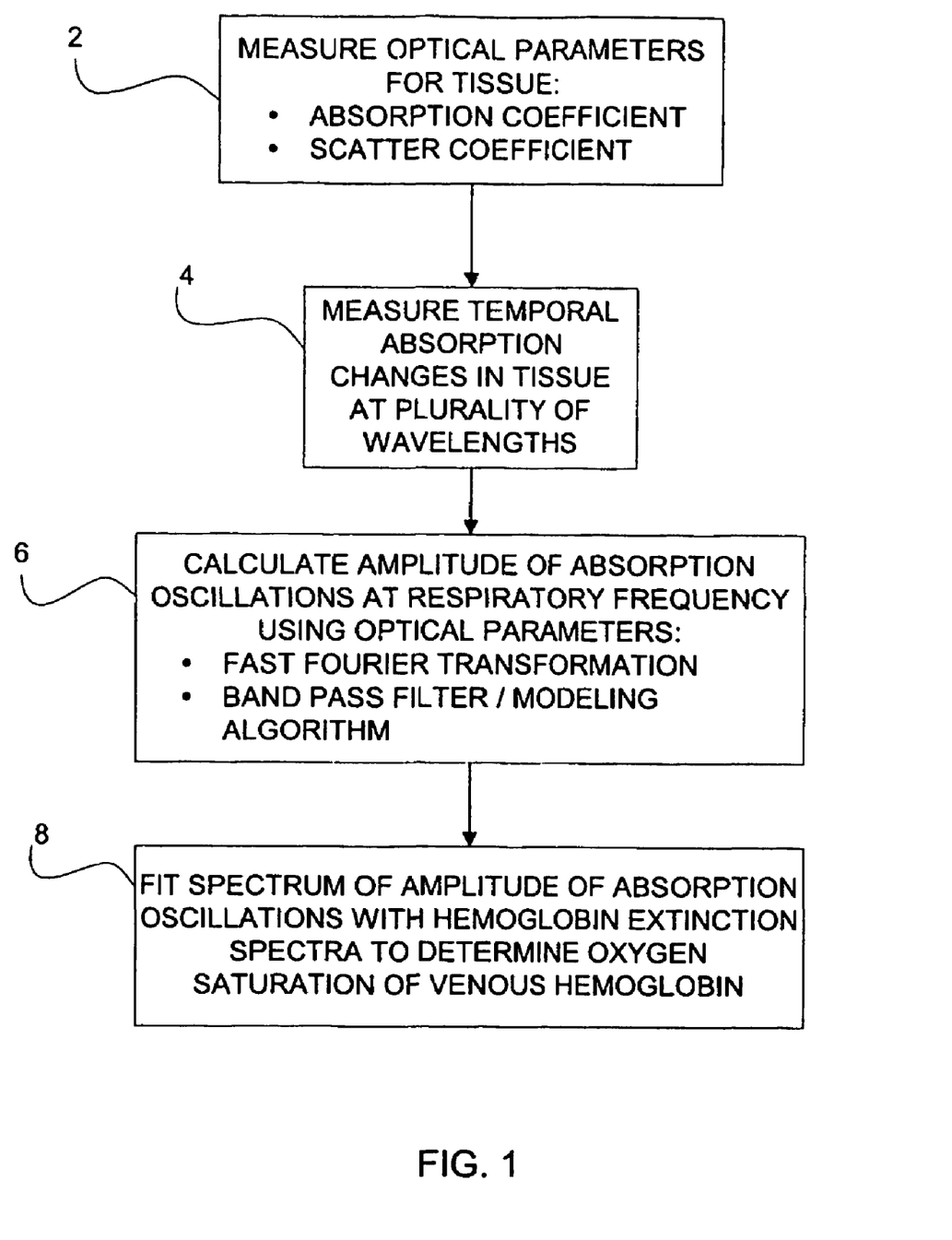
FIG. 1 is a flowchart illustrating in general steps of an invention method embodiment.

Turning now to the drawings, FIG. 1 is a flowchart illustrating in general the steps of an embodiment of the method of the invention. The embodiment of FIG. 1 comprises a step of measuring optical parameters for tissue comprising at least an absorption coefficient $\mu_a$ and a reduced scatter coefficient $\mu_s'$ (block 2). Absorption changes are then measured over time at a plurality of wavelengths (block 4), with at least 2 wavelengths required and at least 8 preferred. Using the optical parameters and the measured absorption changes over time, the amplitudes of absorption oscillations at the respiratory frequency are then calculated (block 6). The spectrum of the experimental absorption amplitude is then fit with a hemoglobin absorption spectrum to determine an oxygen saturation of venous hemoglobin.

Figure 2A:
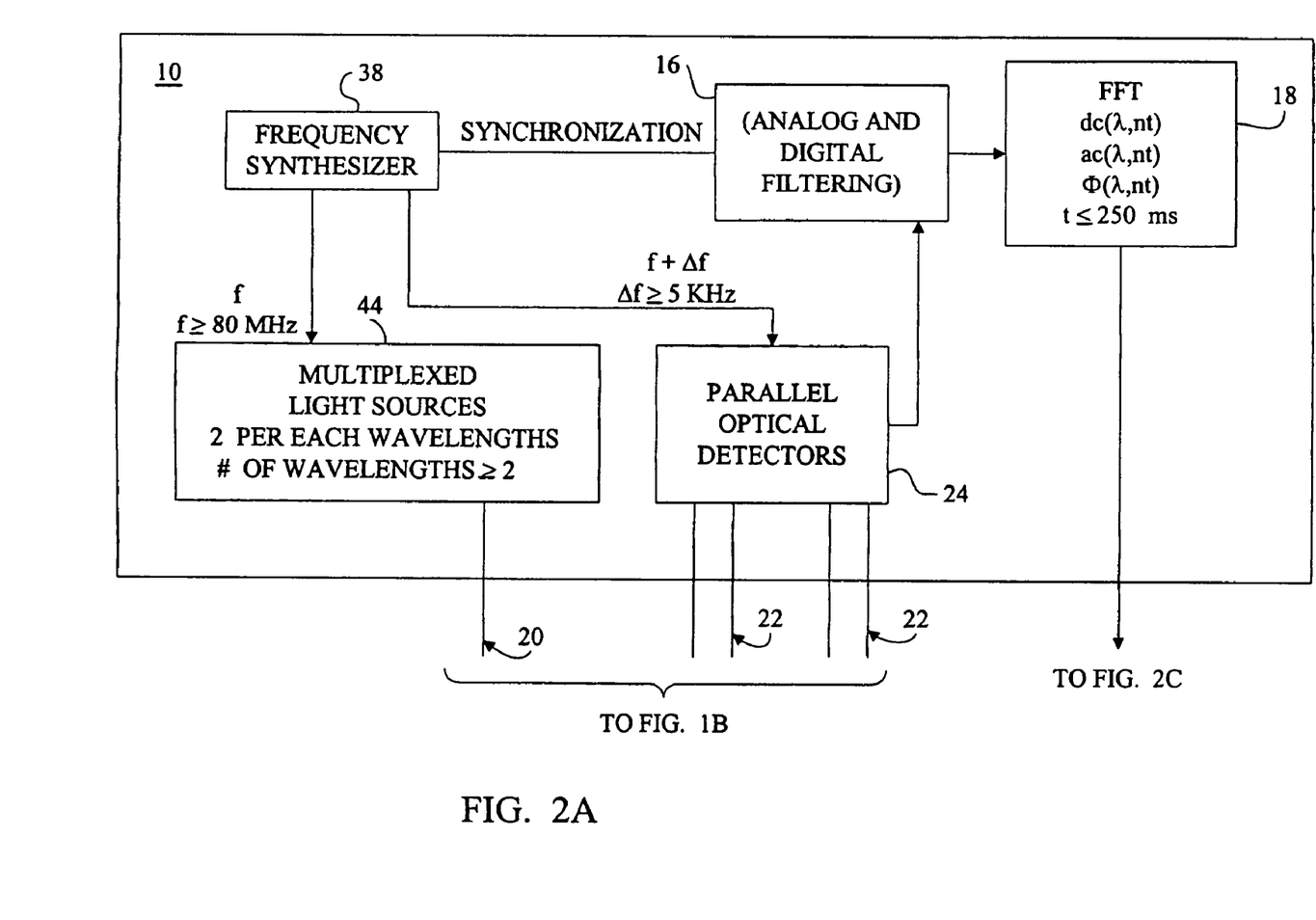
FIG. 2(a)–(c) is a block diagram illustrating a spectrometer device useful for practice with an invention embodiment.
Figure 2B:
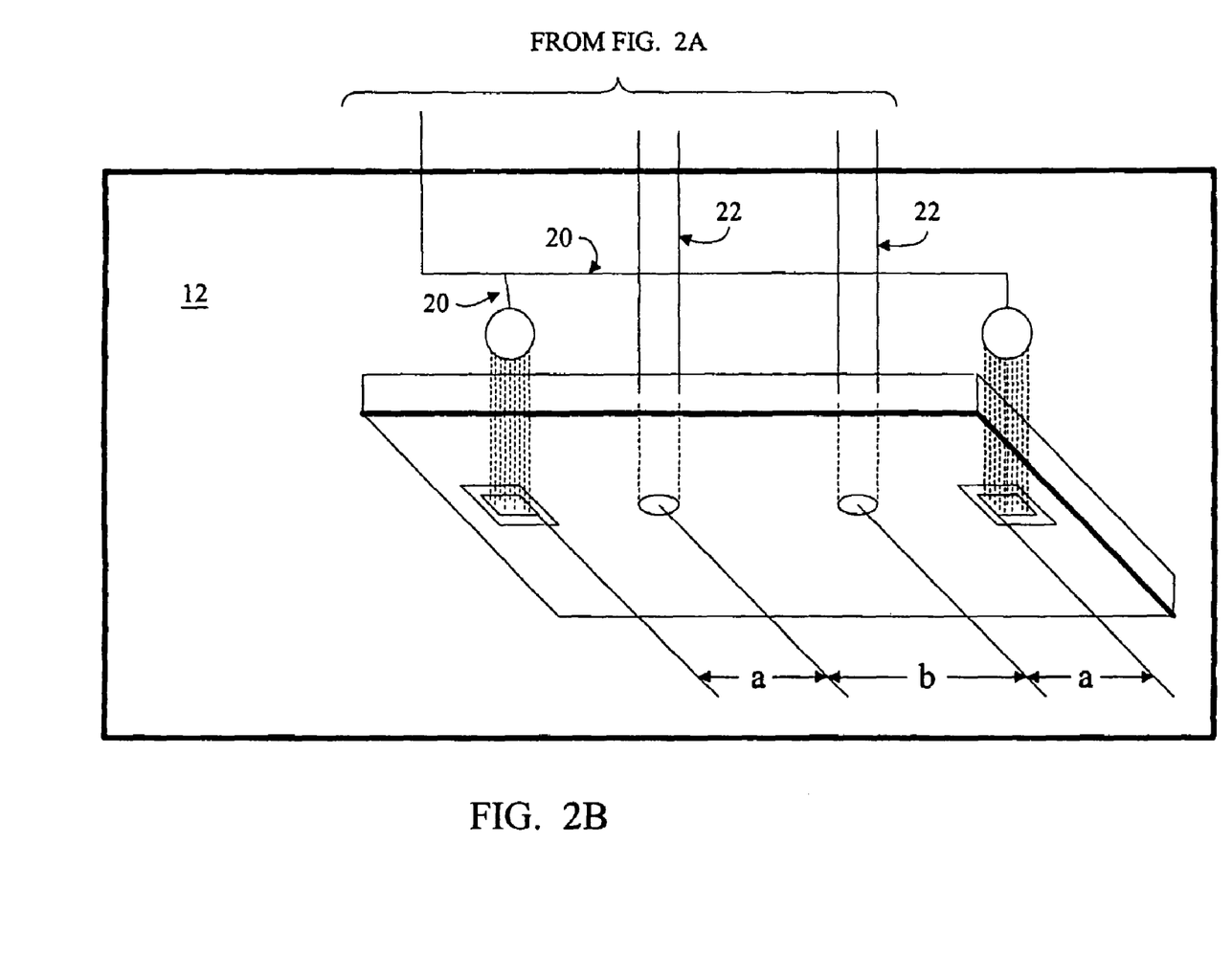
Figure 2C:
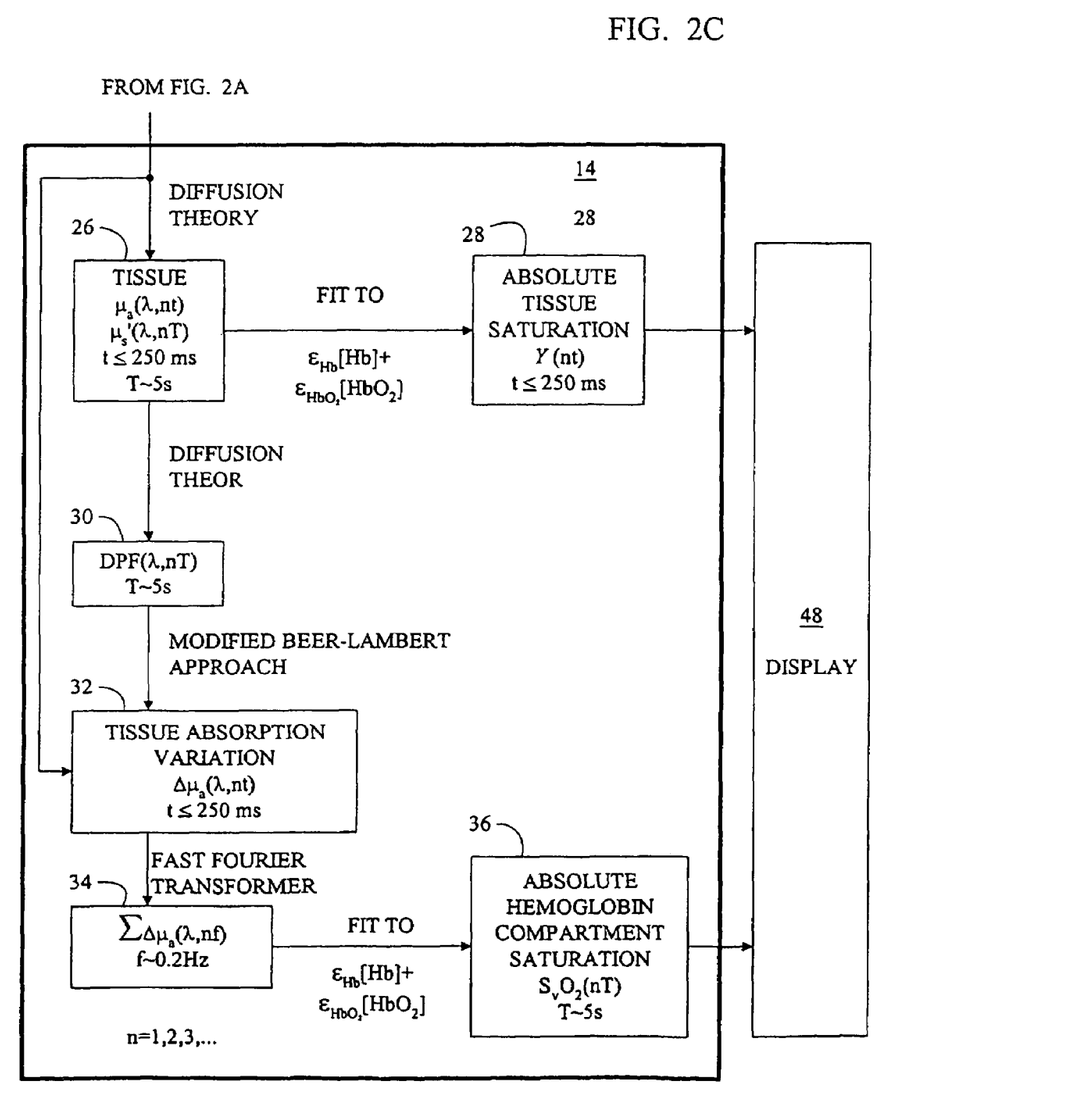

Referring now to FIG. 2(a)–(c), an apparatus for practicing methods of the invention comprises a frequency-domain spectrometer 10 to obtain time-resolved measurements of phase and amplitude. Artisans will appreciate that optical measurements can be performed with either continuous wave methods, i.e., using constant light intensity, or with time-resolved methods. Time-resolved methods include the time-domain where light intensity is pulsed with a pulse width in the order of picoseconds or less, and the frequency-domain, where light intensity is sinusoidally modulated at a radio frequency. In the time-domain, the time-of-flight distribution of detected photons is measured, whereas in the frequency-domain an average intensity, the amplitude, and a phase of a detected modulated intensity are measured. The time-domain and the frequency-domain methods are mathematically related by a temporal Fourier transform. Thus, the time-domain method is equivalent to a collection of frequency-domain measurements over a band of modulation frequencies.

For exemplary purposes, an embodiment of the present invention is described with the frequency-domain approach to measurement of venous hemoglobin saturation. However, the same method described is applicable in the time-domain. One aspect of the invention is the use of a time-resolved optical method, which is performed in either the frequency-domain or the time-domain. Importantly, time-resolved methods allow the separation of reduced scattering and absorption coefficients of tissues. The separation of reduced scattering and absorption coefficients of tissues allows for absolute absorption measurements and, therefore, absolute hemoglobin concentration measurements.

Artisans will appreciate that in frequency-domain spectroscopy the intensity of the light source is modulated at a radio frequency f, preferably 110 MHz, and the detector sensitivity is modulated at a frequency f+Δf, where the offset frequency Δf is lower than f, preferably in the kHz range. It is noted, however, that radio frequencies other than 110 MHz are viable, being limited only by the fact that too low a radio frequency results in inadequate phase shift and too high a radio frequency will be outside a range of known detectors' capabilities.

The frequency-domain spectrometer 10 connects to an optical probe 12 and a processor 14 for analyzing data from the frequency-domain spectrometer 10 and optical probe 12. Detector output is passed through a low-pass filter 16 to a fast Fourier transformer 18 to provide an average intensity (dc), an amplitude (ac), and a phase (Φ), i.e., time-resolved measurement data, of the detected signal at frequency f.

The optical probe 12 preferably contains optical source fibers 20 that guide light to tissue to be examined, and detector fibers 22 that guide the collected light from tissue to an optical detector 24, such as a photo multiplier tube or photo sensor. The probe 12 should preferably be lightweight and partially flexible to adapt to the surface of the examined tissue, but its shape should remain substantially unaltered in order to maintain a well defined and fixed geometrical relationship between the source fibers 20 and detector fibers 22. The optical probe 12 is designed to afford quantitative tissue spectroscopy without requiring any sort of instrumental calibration. To position both the source fibers 20 and detector fibers 22 of the optical probe 12 on the common side of the tissue sample, the invention method uses diffused reflection geometry. This feature allows the optical probe 12 to be applied to any tissue of interest.

To determine a geometrical arrangement of the source fibers 20 and the detector fibers 22, the distance a should be greater than, or in the order of, 1.0 cm to achieve a sufficient optical penetration depth into the tissue. It is noted that this separation distance of about 1.0 cm is less than distances that may be useful for performing arterial measurements (e.g., about 1.5 cm). It has been discovered that a lower optical penetration depth is desirable to achieve a higher sensitivity to superficial veins, which is advantageous for measurement of the venous saturation. In addition, a+b should be less than, or in the order of, 4 cm to collect data with a high signal-to-noise ratio. Moreover, b should assume values between about 0.5 cm and about 2 cm to be large enough to distinguish different signals at separations a and a+b, and small enough to ensure that the signals at separations a and a+b probe essentially the same tissue volume.

Figure 3:
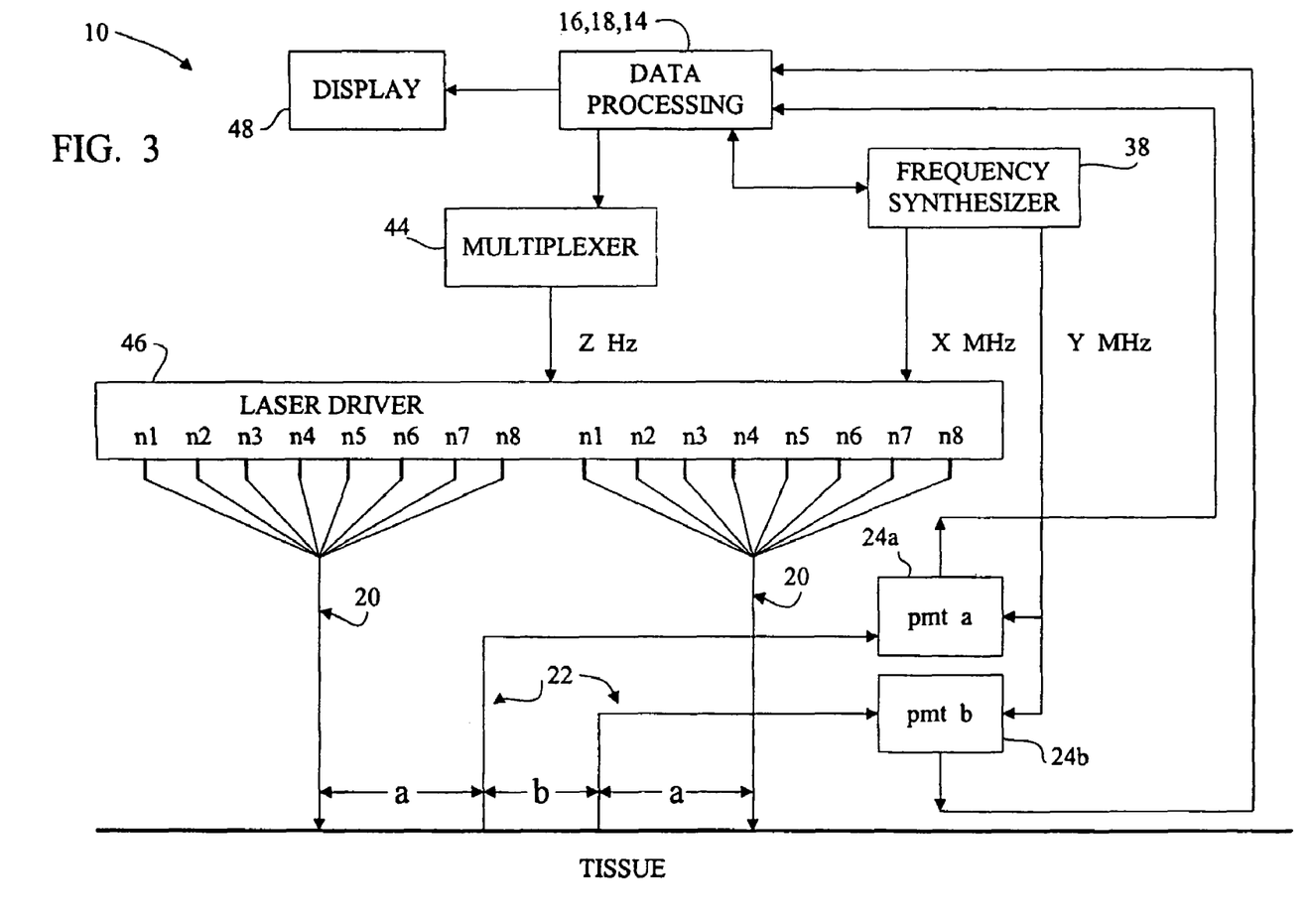
FIG. 3 is a block diagram illustrating a spectrometer device useful for practice with an invention embodiment.

By way of additional description useful for practice of methods of the invention, reference is now drawn to FIG. 3 in addition to FIG. 2. The preferred frequency-domain tissue spectrometer 10 includes a frequency-synthesizer 38 to modulate the intensity of laser diodes at a frequency of x MHz, e.g., 110 MHz. The frequency-synthesizer 38 also modulates a second dynode of two photo multiplier tubes (pmt), pmt a 24a and pmt b 24b, of the optical detector 24 (FIG. 2), at a frequency of y MHz, e.g., 110.005 MHz. An example of a suitable commercially available frequency domain spectrometer is Model No. 96208 available from ISS Inc., Champaign, Ill. Artisans will appreciate that other optical detectors can be used, but pmt's are preferred for their sensitivity.

The frequency-domain spectrometer 10 operates at at least two wavelengths in a range from about 600 to 1000 nm. For exemplary purposes, eight discrete wavelengths n1–n8 (for example 636, 675, 691, 752, 780, 788, 830, 840 nm) may be used in the red and near-infrared spectral region. Artisans will appreciate that other similar wavelengths may be used. It is noted that optical spectroscopy in the wavelength range from 600 to 1000 nm achieves a sufficient photon penetration depth to non-invasively probe macroscopic tissue volumes and remains sensitive to oxygen saturation of hemoglobin.

A multiplexer 44 multiplexes the light sources, two laser diodes contained in a laser driver 46 per each wavelength, at a rate of z Hz, e.g., 100 Hz, to timeshare the two photo multiplier tubes. As a result, 50 cross correlation periods are acquired during the on-time of each laser diode, and a complete acquisition cycle over the eight wavelengths is completed every 80 ms (or 160 ms if two lasers per each wavelength are employed). The multiplexer 44 electronically multiplexes the light sources at a rate z such that N/z≧P/2, with N total number of light sources, and P period of oscillation of the time-varying hemoglobin compartment to be measured. Although practice of an invention method may be accomplished using as few as a single breathing cycle, preferably data is taken over a plurality of breathing cycles, by way of example over about 10 or more cycles. 10–15 cycles has been discovered to be a most preferable range. Because different animals have different breathing cycles, this will result in different numbers of data points being obtained for study of different animals.

As an example, piglets have a breathing cycle of from 0.6–0.9 Hz, with the result that 10–15 cycles occur in a time period of about 20 sec. At a rate of a complete spectrum being measured in 80 ms, then, about 256 data points are taken for piglets over the most preferred 10–15 breathing cycle range. Further, it may be desirable to average successive FFT to obtain more meaningful data. For example, in a study of piglets it may be desirable to average about 800 successive fast Fourier transformations, with each computed from a data set shifted by one data point with respect to the previous one. Accordingly, a total of about 1,000 data points may be taken to correspond to one venous saturation reading corresponding to a data train of 80 s in length. Humans have a lower breathing frequency of about 0.22–0.26 Hz, with a result that about 40–60 seconds are required for 10–15 breathing cycles to occur. At a rate of 80 ms for a spectrum to be measured, about 750 data points are required. Again, it may be desirable to obtain these data points from averaging a larger number of consecutive fast Fourier transformation points.

Each one of sixteen laser diodes is coupled to an optical fiber approximately 400 $\mu$m in core diameter. The preferred embodiment groups the two sets of eight fibers guiding light at the eight wavelengths into two source fiber bundles 20 having a rectangular section of internal size, for example, 3.5×1.2 mm². The optical signal detected on tissue is guided to two parallel detector channels of the spectrometer by two optical detector fiber bundles 22, for example, 3 mm in internal diameter. The source fibers 20 and the detector fibers 22 are placed on the common side of the examined tissue, for example a forehead, in the symmetrical configuration shown in FIG. 3.

As discussed above with reference to FIG. 2 above, this geometrical arrangement of the source fiber 20 and the detector fibers 22 features four distinct source-detector pairs, and two distinct source-detector separations (a and a+b, e.g., 1 cm and 2 cm, respectively). Artisans will appreciate that other distances between the source and detector fibers are contemplated. The outputs of pmt a 24a and pmt b 24b are processed in the data processing apparatus 16, 18, 14, as seen in FIG. 3, and the results are provided in a display 48.

This source-detector configuration affords quantitative spectroscopy independent of source, detector, and optical-coupling terms, i.e., without requiring instrumental calibration. To avoid pre-calibration, the present invention relies on a physical model to quantitatively describe the relationship between the collected optical signal and tissue optical properties. This model, which assumes a macroscopically uniform distribution of the time-varying hemoglobin compartment in tissue, is well justified in most cases, but there may be cases where its assumptions are not fulfilled. To maximize the signal-to-noise ratio, the calculation of $\mu_a'$ may be regularly updated; e.g. every 10 seconds. In this way, the contribution of the phase noise to the measurement of $\mu_a$ is strongly reduced, whereas the acquisition time for the absorption spectrum is maintained.

Referring now to the process of data analysis, the processor 14 operates so that a respiratory component of tissue absorption can be quantified to produce absolute values of time-varying hemoglobin compartment and/or tissue saturation. A first step of the analysis consists of a quantitative determination of a tissue reduced scattering coefficient ($\mu_s'$) and an absorption coefficient ($\mu_a$) (block 26 in FIG. 2). To this aim, a multi-distance method is applied using two or more source-detector separation distances (a and a+b). This is achieved by using multiple sources either multiplexed or modulated at different frequencies to electronically distinguish the corresponding signals and/or multiple detectors which can acquire data in parallel, or sequentially. Additionally, this can be achieved by moving a source with respect to a detector over the desired range of source-detector separation.

The multi-distance time-resolved measurement method assumes a homogeneous and semi-infinite geometry. The absolute values of the absorption ($\mu_a$) and reduced scattering ($\mu_s'$) coefficients of tissue are given in terms of the dc, ac, and phase slopes versus source-detector separation ($S_{dc}$, $S_{ac}$, and $S_\Phi$, respectively). In particular, either the $S_{dc}$ and $S_\Phi$ pair, or the $S_{ac}$ and $S_\Phi$ pair can be used to measure $\mu_a$ and $\mu_s'$. Using dc and phase:

$$\mu_s' = \frac{2\nu}{3\omega} S_\Phi (S_\Phi^2 + S_{dc}^2)^{\frac{1}{2}} \qquad \mu_a = \frac{S_{dc}^2}{3\mu_s'}$$

using ac and phase:

$$\mu'_s = -\frac{2v}{3\omega} S_\Phi \quad S_{ac} \quad \mu_a = \frac{S_{ac}^2}{3\,\mu'_s}\left[1 - \left(\frac{3}{2}\frac{\omega\mu'_s}{vS_{ac}^2}\right)^2\right]$$

where ω is the angular modulation frequency of the source intensity, and v is the speed of light in tissue. More information regarding the application of a multi-distance method may be had by reference to "*Quantitative Determination of the Absorption Spectra of Chromophores in Strongly Scattering Media: a Light-Emitting-Diode Based Technique,*" by Fantini et al., Appl. Opt. 33: 5204–5213, 1994; which is incorporated herein by reference.

The present method averages the $\mu_s'$ measurement on a time scale T, which is longer than a data acquisition time t, where the data acquisition time t is equal to or less than about one-half a period of oscillation. For example, for a data acquisition time of t>250 ms, a $\mu_s'$ measurement time T is approximately 5 seconds. The longer time scale allows the present invention to maintain a high temporal resolution in the absorption measurement, while drastically reducing the contribution of the phase noise because the phase data only appears in the expression for $\mu_s'$ which is averaged over time T. The only assumption of this method is that the reduced scattering coefficient $\mu_s'$ does not vary on a time scale faster than T, which is generally true for T in the order of a few seconds.

To measure tissue saturation Y, the spectrum of the tissue absorption is fit with a linear combination of the extinction spectra of oxygenated hemoglobin and deoxygenated hemoglobin. The fitted parameters are the concentrations of oxygenated hemoglobin ([HbO$_2$]) and deoxygenated hemoglobin ([Hb]). Tissue saturation Y is then given by the expression [HbO$_2$]$_t$/([HbO$_2$]$_t$+[Hb]$_t$), where the subscript "t" indicates that the involved concentrations refer to tissue (block 28). Since tissue saturation Y is determined by absorption $\mu_a$ and not by scattering $\mu_s'$, the present invention achieves an absolute measurement of tissue saturation Y with a fast temporal resolution and having excellent signal-to-noise ratio characteristics.

In addition to the above measured tissue saturation Y, the time-resolved measurements may be used to simultaneously measure the time-varying hemoglobin venous compartment (SvO$_2$). The venous hemoglobin concentration in tissue oscillates with time as a result of the respiration induced volume changes in the venous compartment. When a subject inspires the chest cavity is expanded as air enters and fills the lungs. This expansion is associated with a decrease in the intrathoracic pressure that in turn causes an increased venous return because of the increased pressure gradient between peripheral and intrathoracic veins. As a result, the volume of hemoglobin in the peripheral venous compartment decreases. As the subject expires, the chest cavity contracts, the intrathoracic pressure is increased, venous return is decreased, and the peripheral venous compartment expands. Hemoglobin volume correspondingly increases in the peripheral venous compartment. Consequently, the detected oscillations in the optical signal at the respiratory frequency can be assigned to the venous hemoglobin compartment. A venous compartment saturation can then be related to the oscillatory components of the absorption coefficients at two or more wavelengths.

To perform absolute venous oximetry using the time-resolved measurements, the amplitude of the respiration-induced absorption oscillations is quantitatively measured. Embodiments of the present invention comprise use of a modified Beer-Lambert law approach to translate the temporal intensity ratio collected at each wavelength [I(λ,t)/I(λ,0)] at a known distance (e.g., 1 cm) from the illumination point, into a time variation in the tissue absorption [Δ$\mu_a$(λ,t)]. More information regarding the application of a modified Beer-Lambert law approach may be had by reference to "*Estimation of Optical Pathlength through Tissue from Direct Time of Flight Measurement*", by Delpy et al., Phys. Med. Biol. 33:1433–1442, 1988; which is incorporated herein by reference.

This approach may be implemented by applying:

$$\Delta\mu_a = (\lambda, t) = \frac{1}{L_{eff}} \ln\left[\frac{I(\lambda, 0)}{I(\lambda, t)}\right]$$

where $L_{eff}$ is the effective optical pathlength from the illuminating point to the light collection point. $L_{eff}$ is given in terms of the tissue absorption coefficient ($\mu_a$) and tissue scatter coefficient ($\mu_s'$) and the source detector separation r in a semi-infinite turbid medium (where the illumination and collection points are at the boundary of the turbid medium) by:

$$L_{eff} = \frac{3\mu_s' r^2}{2\left(r\sqrt{(3\mu_a\mu_s')} + 1\right)}$$

Application of this relationship indicates that for typical values of the near-infrared absorption and reduced scattering coefficients of tissues (e.g., $\mu_a$=0.1 cm$^{-1}$, and ($\mu_s'$=10 cm$^{-1}$), the value of $L_{eff}$ is about 5.5 cm for r=1 cm.

A multi-distance measurement scheme may be implemented using data collected by fiber bundle detectors 22 located at two distances (e.g., 1.0 and 2.0 cm) from the source fiber bundle 20. At these source-detector distances, light propagation in tissues occurs according to a diffusion regime as per studies previously reported in the literature (see, e.g., "*Effective Source Term in the Diffusion Equation for Photon Transport in Turbid Media*", by Fantini et al., Appl. Opt. 36: 156–163 (1997); incorporated herein by reference). Those knowledgeable in the art will appreciate that empirical methods are available as an alternative to the diffusion equation model to describe the spatial dependence of the optical signal. In general, the different sensitivity of the two channels may be accounted for through a preliminary calibration measurement on a tissue-like sample.

The present invention further comprises data processing steps for evaluating the amplitude of the respiration-induced absorption oscillations. One invention embodiment comprises data processing steps of calculating amplitudes through a Fourier transform, and preferably a fast Fourier transform (FFT), of Δ$\mu_a$ at the respiration frequency (blocks 32 and 34 in FIG. 2). The sum of the amplitudes of the FFT Δ$\mu_a$ over the respiratory frequency band yields a measure of the amplitude of the respiration induced absorption oscillations. This method assumes that the Fourier spectrum of Δ$\mu_a$ shows a discernable peak at the respiratory frequency. The FFT requires multiple respiration cycles to produce a venous saturation reading. Of the order of 10–15 respiration cycles are preferred.

A second invention embodiment comprises data processing steps for computing the amplitude of the respiratory induced absorption oscillations through use of a band pass filter in combination with using a modeling algorithm. The band pass filter serves the purpose of isolating the absorption oscillations at the respiratory frequency by suppressing higher and lower frequency components in $\Delta\mu_a$. A preferred modeling algorithm comprises a sin-wave model fit to each respiratory cycle. The amplitude of the fitted sin wave gives an estimate of the absorption oscillation amplitude The FFT and the band pass filter methods each have characteristics that may make one or the other set of data processing steps preferable over the other under particular circumstances. The major advantage of the band pass filter method is that it can achieve a venous saturation reading from each individual respiratory cycle. The FFT method, on the other hand, requires data from multiple respiratory cycles to produce venous saturation readings. Consequently, the band pass filter method is particularly effective during transients. The band pass filter method, on the other hand, is also susceptible to error from fluctuations in the respiratory frequency and/or from irregular respiration patterns. The FFT method proves much more robust in these instances, as the irregular effects are averaged out over the multiple respiratory cycles measured.

With these considerations in mind, care should be taken in choosing which method to use. If a venous saturation level is to be measured that will involve changes induced by exercise, for instance, the band pass filter method may be preferred as it will more clearly represent changing saturation levels. If a subject is to be measured at rest or where venous saturation is otherwise expected to be in a relatively steady state, on the other hand, the FFT method may be preferred.

Once the amplitude of the oscillations has been computed, regardless of the method used, the spectrum of the absorption oscillations at the respiratory frequency must be fit to determine time varying hemoglobin saturation levels. The present invention fits the spectrum with a linear combination of the extinction spectra of oxygenated hemoglobin and deoxygenated hemoglobin: $[\epsilon^{HbO2}(\lambda_i)\Delta[HbO_2]^{RESP}+\epsilon_{Hb}(\lambda_i)\Delta[Hb]^{RESP}]$, where $\epsilon_{HbO2}(\lambda_i)$ and $\epsilon_{Hb}(\lambda_i)$ are the extinction coefficients of oxygenated and deoxygenated hemoglobin, respectively. The fitted parameters are the oscillatory concentrations of oxygenated hemoglobin ($[HbO_2]^{RESP}$) and deoxygenated hemoglobin ($[Hb]^{RESP}$) at the respiratory frequency. The venous hemoglobin saturation is then given by the expression $[HbO_2]^{RESP}/([HbO_2]^{RESP}+[Hb]^{RESP})$, where the superscript "RESP" indicates the respiration origin (block 36).

The minimization of the sum of the squares of the residuals (i.e., $\Sigma_i[\Delta\mu_a^{(fit)}(\lambda_i)-\Delta\mu_a^{(resp)}(\lambda_i)]^2$) yields a linear system whose solution gives the best fit concentrations of amplitude of the oscillatory oxy-and deoxy-hemoglobin concentrations shown below by EQTN. 1. The oxygen saturation of the hemoglobin compartment oscillating synchronously with respiration (SvO$_2$-NIRS) is then given by EQTN 2 shown below.

$$\Delta[HbO_2]^{(resp)} = \frac{\left(\sum_i \Delta\mu_a^{(resp)}(\lambda_i)\varepsilon_{HbO2}(\lambda_i)\right)\left(\sum_i \varepsilon_{Hb}^2(\lambda_i)\right) - \left(\sum_i \Delta\mu_a^{(resp)}(\lambda_i)\varepsilon_{Hb}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)} \quad \text{EQTN. 1}$$

$$\Delta[Hb]^{(resp)} = \frac{\left(\sum_i \Delta\mu_a^{(resp)}(\lambda_i)\varepsilon_{Hb}(\lambda_i)\right)\left(\sum_i \varepsilon_{HbO2}^2(\lambda_i)\right) - \left(\sum_i \Delta\mu_a^{(resp)}(\lambda_i)\varepsilon_{HbO2}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2}$$

$$S_V O_2 - NIRS_{resp} = \frac{\Delta[HbO_2]^{(resp)}}{\Delta[HbO_2]^{(resp)} + \Delta[Hb]^{(resp)}} = \quad \text{EQTN. 2}$$

$$\frac{\left(\sum_i \Delta\mu_a^{(resp)}(\lambda_i)\varepsilon_{HbO2}(\lambda_i)\right)\left(\sum_i \varepsilon_{Hb}^2(\lambda_i)\right) - \left(\sum_i \Delta\mu_a^{(resp)}(\lambda_i)\varepsilon_{Hb}(\lambda_i)\right)\left(\sum_i \varepsilon_{HbO2}(\lambda_i)\varepsilon_{Hb}(\lambda_i)\right)}{\left(\sum_i \Delta\mu_a^{(resp)}(\lambda_i)\varepsilon_{HbO2}(\lambda_i)\right)\left(\sum_i \varepsilon_{Hb}(\lambda_i)[\varepsilon_{Hb}(\lambda_i) - \varepsilon_{HbO2}(\lambda_i)]\right) - \left(\sum_i \Delta\mu_a^{(resp)}(\lambda_i)\varepsilon_{Hb}(\lambda_i)\right)\left(\sum_i \varepsilon_{HbO2}(\lambda_i)[\varepsilon_{Hb}(\lambda_i) - \varepsilon_{HbO2}(\lambda_1)]\right)}$$

It is noted that for the determination of SvO$_2$-NIRS$_{resp}$, L$_{eff}$ is only required to within a wavelength-independent factor. In fact, the above equation shows that a common, wavelength independent multiplicative factor in $\Delta\mu_a(\lambda_i)$ cancels out in the expression for SvO$_2$-NIRS$_{resp}$. By contrast, the wavelength dependence of L$_{eff}$ is important for the measurement of venous saturation with the present method. Accordingly, L$_{eff}$ is preferably measured at each wavelength using the multi-distance, frequency-domain technique.

It is also noted that in order for the calculation of this method embodiment to be correct, it is required that: (1) the oscillations of $\mu_a$ at the respiratory frequency can be reliably attributed to hemoglobin (and not, for instance, to motion artifacts); (2) the hemoglobin-concentration fluctuations result from the volume oscillation of a hemoglobin compartment rather than from periodic fluctuations in the blood flow; and (3) the fluctuating hemoglobin compartment responsible for the measured $\Delta\mu_a$ is the venous compartment. Embodiments of the present invention provide steps for addressing these three requirements.

It will be appreciated that steps taken to address these three points may generally be referred to as "verification steps". That is, insuring that measurements meet with any or all of the three requirements of points (1)–(3) may be considered a verification of the accuracy of the measurements. Further, it will be appreciated that these verification steps will be of utility for other method embodiments that may comprise different particular calculational methods. Indeed, a level of uncertainty exists with virtually any method for optical venous saturation measurement. For example, it is known that respiratory sinus arrhythmia, which is present in all healthy human subjects, induces fluctuations in the arterial compartment at the respiratory frequency. These fluctuations can confound the isolation of the venous saturation level at the respiration frequency. Thus methods that rely on measurement of respiratory oscillations have an uncertainty associated with them regarding potential arterial compartment contribution.

Figure 4:
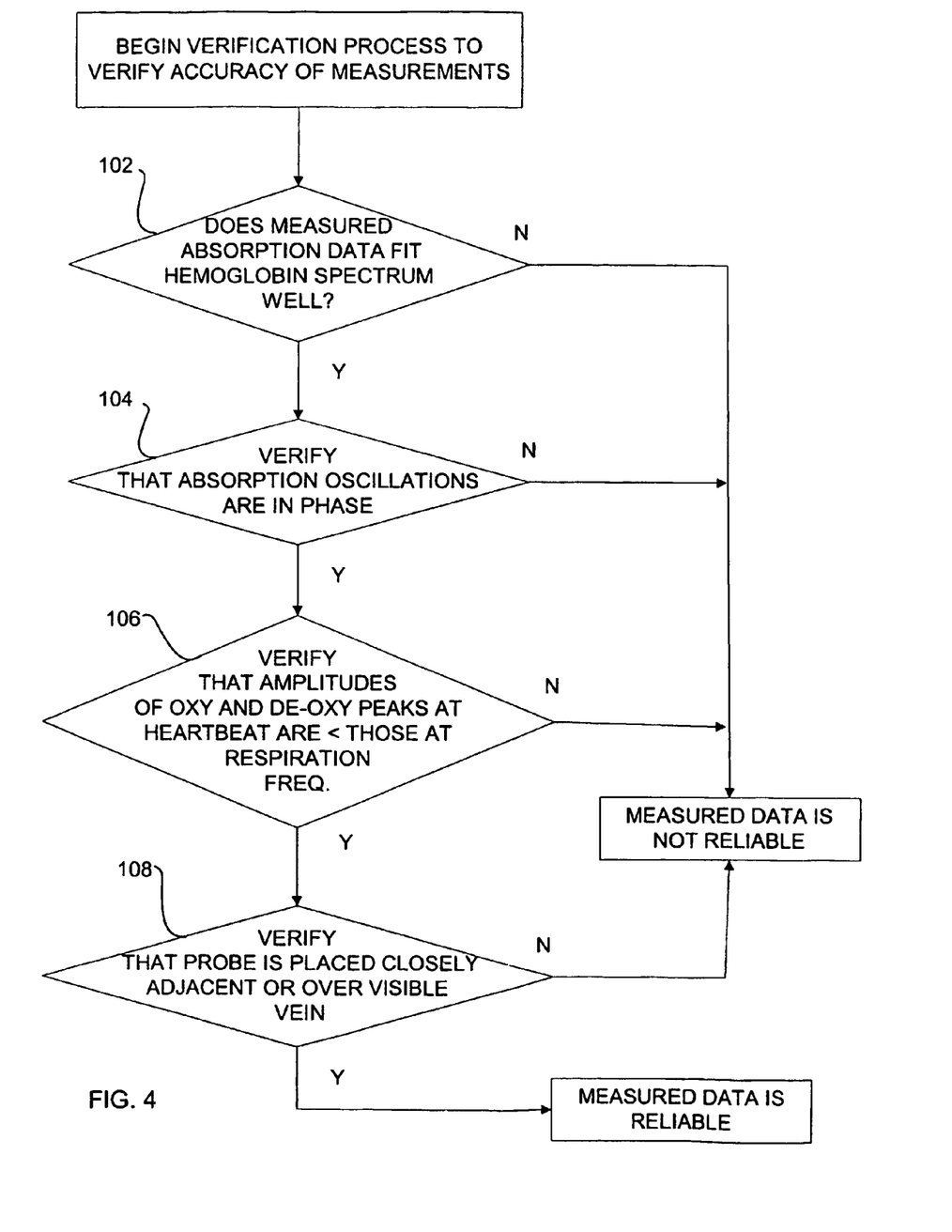
FIG. 4 is a flow chart illustrating example verification steps of invention embodiments.

FIG. 4 is a flowchart illustrating some of the various verification steps contemplated by methods of the present invention to insure measurement accuracy. It will be appreciated that the flowchart of FIG. 4 presents these steps in series for purposes of convenience only, and that different method embodiments may comprise using any particular order or number of verification steps. By way of example, different method embodiments may comprise using only one of these verification steps.

With reference now drawn to FIG. 4, one verification step 102 comprises requiring that the hemoglobin spectrum closely fits or matches the absorption data relatively well. It will be appreciated that such a determination will be of particular use in addressing point (1) above, i.e. that measured oscillations result from hemoglobin. Those knowledgeable in the art will also appreciate that there are a variety of methods for determining whether two data sets "closely fit or match one another". For example, a visual comparison between output data can be indicative of a close match. Also, a variety of calculational comparison methods are available. A comparison can be made between the residuals and the experimental error in the absorption data. By way of a more particular example, one example of this step 102 may comprise requiring that the absolute value of the relative residuals be at most twice the experimental percent error in absorption data. A second example step 102 may comprise analyzing the standard deviation of data collected over a plurality of points, and discarding samples having an unacceptably high standard deviation. For example, absorption values obtained over several hundred successive Fourier transformation data points may be analyzed to estimate the error. Data having a standard deviation error greater than 15% or some other suitable level may be discarded.

An additional verification step 104 comprises verifying that the absorption oscillations at different wavelengths are in phase with one another. Preferably, this should be done for each pair of the plurality of wavelengths measured. In-phase measurements confirm that the oscillations are a result of volume fluctuations and not flow fluctuations. That is, if absorption oscillations are not in phase, then the oxygenated and deoxygenated hemoglobin oscillations are not in phase, which suggests that what is being measured results from a blood flow fluctuation due to an increased rate of blood inflow of oxygenated hemoglobin and outflow of deoxygenated hemoglobin. Oscillations in phase, on the other hand, suggest that what is being measured is a volume fluctuation as opposed to a flow fluctuation. As a result, in-phase absorption oscillations confirm that the oxygen saturation of a time-varying hemoglobin compartment is being measured.

Still another verification step 106 comprises verifying that the amplitudes of the measured oxygenated and deoxygenated hemoglobin concentration peaks at the heartbeat frequency are less than those at the respiratory frequency. This provides an objective verification to insure that the venous compartment dominates measurements.

Yet another verification step 108 of a method embodiment comprises verifying that the spectrometer probe is placed closely adjacent, and preferably directly over, a visible vein. Experiments conducted indicate that when the probe is placed directly over a visible vein it is substantially more likely that the measured oscillations result from venous contributions than when the probe is placed not adjacent to a vein. It is noted that in computer program product embodiments of the present invention, this step may be carried out through a query of the user, or through detection means.

Figures 5, 5A, 5B:
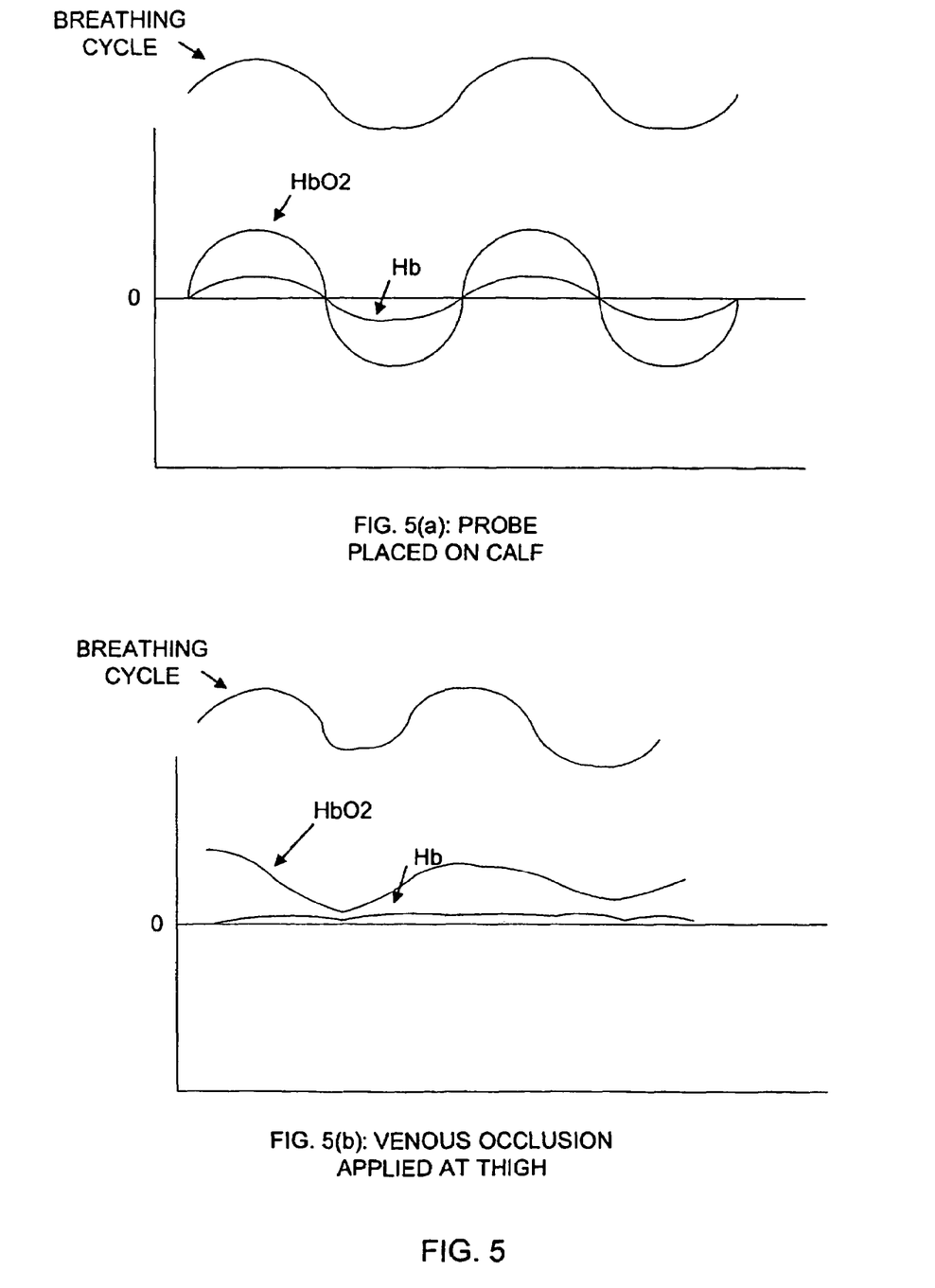
FIG. 5(a)–(b) are graphs useful for illustrating measurement verification steps of an invention embodiment.

FIG. 5 is useful in illustrating results of this verification step. FIG. 5(a) illustrates oscillation measurements made using a method embodiment of the present invention on the calf of a human subject, with the probe placed over a visible vein. In particular, FIG. 5(a) illustrates a summary of measurement of deoxygenated hemoglobin (Hb) and oxygenated hemoglobin ($HbO_2$), with the oscillations appearing in phase with the respiratory cycle. Without moving the probe, a venous occlusion was placed on the thigh of the subject to suppress venous compartment volume fluctuations. Resulting data are summarized in FIG. 5(b), confirming that the venous compartment is dominating measurements, as the oscillations of oxygenated and deoxygenated hemoglobin are suppressed during venous occlusion even though no blockage of the arteries occurs. It is noted that FIGS. 5(a) and (b) are data plots representative of data following processing with one of the amplitude calculation methods of the invention, e.g., after application of a band pass filter and fitting with a sin wave algorithm.

It has been discovered that the novel method of the invention, preferably comprising one or more of the verification steps, allows for accurate measurements of venous oxygenation saturation levels to be made without requiring mechanical ventilation, venous occlusions, or other additional required elements of methods of the prior art. It is noted that it may be desirable when using a method of the invention with a human subject to use a metronome or other patient frequency guide to regulate breathing frequency.

The novel methods of the present invention were tested on a number of subjects including piglets and humans. In addition to the method of the present invention, for comparison purposes the test subjects were likewise subjected to known venous saturation measurement methods of the prior art using venous occlusions and/or invasive measurements. Generally these tests indicated very good agreement between venous saturation levels determined through methods of the present invention as compared to results obtained through methods of the prior art.

The tests' results also provide some useful guidance regarding practice of various aspects of the present invention. For instance, the tests offer a comparison between use of FFT and band pass filter data processing steps. Consistent with the discussion regarding the two methods made herein above, it was generally observed that the band pass filter method has significant advantages in terms of its ability to detect transients and/or changing saturation levels. Because it is averaged over multiple respiration cycles, the FFT method was found to be fairly robust during steady state conditions.

Also, the tests highlighted the importance of steps of the invention related to verifying that the venous compartment contributions dominated the respiratory oscillations being measured. As discussed above, this can be accomplished through one or more of a number of potential verification steps, including for example by placing the probe on top of a visible vein, by verifying that the respiratory oxygenated and deoxygenated hemoglobin oscillations are in phase, and by verifying that the oxygenated and deoxygenated oscillations have a greater integrated amplitude at the respiratory frequency than at the heartbeat frequency. These verification steps can be used to greatly increase the confidence level in optical venous saturation measurements.

Those knowledgeable in the art will also appreciate that the present invention is well suited for practice in the form of a computer program product. Accordingly, it will be appreciated that additional embodiments of the invention comprise computer program products. These computer program product embodiments comprise computer executable instructions stored in a computer readable medium that when executed cause the computer to perform prescribed actions. Generally, the computer program product embodiments of the invention cause a computer to perform the steps of method embodiments of the invention. Accordingly, it will be appreciated that discussion made herein regarding method embodiments may likewise apply to computer program product embodiments.

Examples of computer readable mediums comprise memories such as magnetic or optical disks and the like, electronic circuitry, embedded circuitry, RAM, ROM, EPROM, SDRAM, and the like. Also, it will be appreciated that the term "computer" as used herein is intended to broadly refer to processor based devices capable of executing instructions. Accordingly, examples of "computers" as used herein may comprise, but are not limited to, personal computers, hand held devices, mainframe computers, processor based instrumentation such as spectrometers, processor based data acquisition and control devices, and the like.

It will also be appreciated that some of the measurement and data processing aspects of the present invention are consistent with those disclosed in U.S. Pat. No. 6,216,021 issued Apr. 10, 2001 to Franceschini et al. (the '021 patent), which has been incorporated herein by reference. While description has been given herein to enable practice of the known best modes of methods of the present invention, additional useful information regarding some consistent aspects, such as measurement and data processing steps, of the present invention may be had through reference to the '021 patent.

From the foregoing description, it should be understood that improved methods have been shown and described which have many desirable attributes and advantages. For example, a time-resolved measurement approach is presented to non-invasively measure the absolute value of time-varying hemoglobin venous compartment saturation without requiring mechanical ventilation or venous occlusion. Other alterations and modifications will be apparent to those skilled in the art. Accordingly, the scope of the invention is not limited to the specific embodiments used to illustrate the principles of the invention. Instead, the scope of the invention is properly determined by reference to the appended claims and any legal equivalents thereof.

What is claimed is:

1. A method for measuring the venous oxygen saturation comprising the steps of:
    illuminating an area of tissue of a subject with intensity modulated light at at least two wavelengths, said subject being free from mechanical ventilation devices and free from venous perturbations
    sensing diffusely reflected light caused by said illumination to acquire time resolved measurement data; and
    processing said time resolved measurement data to determine the absolute saturation of the venous compartment, said processing comprising at least determining an amplitude of respiration induced absorption oscillations.

2. A method for measuring the venous oxygen saturation as in claim 1 wherein:
    the processing step comprises determining at least amplitudes for oxygenated and deoxygenated hemoglobin oscillations at the respiratory frequency.

3. A method for measuring the venous oxygen saturation as in claim 1 wherein:
    the step of sensing diffusely reflected light comprises sensing diffusely reflected light at a plurality of wavelengths; and wherein
    the processing step comprises determining an amplitude of respiration induced absorption oscillations at each of said plurality of wavelengths.

4. A method for measuring the venous oxygen saturation as in claim 3 wherein said plurality of wavelengths comprises at least eight.

5. A method for measuring the venous oxygen saturation as in claim 1 wherein:
    the processing step comprises quantifying said amplitude of absorption oscillations at said respiratory frequency using a fast Fourier transformation.

6. A method for measuring the venous oxygen saturation as in claim 5 wherein the method comprises acquiring time resolved measurement data over at least 10 respiratory cycles.

7. A method for measuring the venous oxygen saturation as in claim 1 wherein:
    the processing step comprises quantifying said amplitude of absorption oscillations at said respiratory frequency by using a band pass filter to isolate said absorption oscillations at said respiratory frequency and subsequently applying a modeling algorithm to said absorption oscillations over each respiratory cycle.

8. A method for measuring the venous oxygen saturation as in claim 7 wherein said modeling algorithm comprises a sin wave fitting algorithm.

9. A method for measuring the venous oxygen saturation as in claim 1 wherein the method further comprises the step of verifying that said absorption oscillations at said at least two wavelengths occur in phase at said respiratory frequency.

10. A method for measuring the venous oxygen saturation as in claim 1 wherein the method further comprises placing a probe on said area of tissue, said probe for generating said intensity modulated light for illuminating said area of tissue, and wherein said probe is placed directly over a visible vein.

11. A method for measuring the venous oxygen saturation as in claim 1 wherein the step of processing said time resolved measurement data comprises determining an amplitude of absorption oscillations at the heartbeat frequency and verifying that the amplitude of said heartbeat frequency absorption oscillations is less than the amplitude of said respiration induced absorption oscillations.

12. A method for measuring the venous oxygen saturation as in claim 1 wherein the step of processing said time resolved measurement data comprises determining absorption data, and wherein the method further comprises verifying that a hemoglobin spectrum closely agrees with said absorption data.

13. A method for measuring the venous oxygen saturation as in claim 1 wherein said steps of illuminating and sensing are conducted on a common side of said area of tissue.

14. A method for measuring the venous oxygen saturation as in claim 1 wherein said processing step comprises fitting said amplitude of respiration induced absorption oscillations with a linear combination of extinction spectra of oxygenated and deoxygenated hemoglobin.

15. A method for measuring the venous oxygen saturation as in claim 1 wherein said processing step comprises determining an effective optical path length between an illumination source and an illuminated point in said illuminated area of tissue, said effective optical path length being used to determine said amplitude of respiration induced absorption oscillations.

16. A method for measuring the venous oxygen saturation as in claim 1 wherein said processing step comprises determining a tissue scattering coefficient and a tissue absorption coefficient, said scattering coefficient and said absorption coefficient being used to determine said amplitude of respiration induced absorption oscillations.

17. A method for measuring the venous oxygen saturation as in claim 1 wherein the time resolved data processing step comprises:
   determining a reduced scattering coefficient and an absorption coefficient for said tissue; and
   using said reduced scattering coefficient and said absorption coefficient to determine an effective optical path length between an illumination source and an illuminated point in said illuminated area of tissue, said effective optical path length being used to determine said amplitude of respiration induced absorption oscillations.

18. A method for measuring a venous oxygen saturation comprising the steps of:
   illuminating an area of tissue of a subject with intensity modulated light in the visible and near infrared spectral range at at least two wavelengths on a common side of said area of tissue;
   sensing diffusely reflected light caused by said illumination to acquire time resolved measurement data for each of said at least two wavelengths; and
   processing said time resolved measurement data at each of said at least two wavelengths to determine the absolute saturation of the venous compartment, said processing comprising determining a reduced scattering coefficient and an oscillation absorption coefficient, quantifying an amplitude of respiration induced absorption oscillations using said reduced scattering coefficient and said oscillation absorption coefficient and using one of either a Fourier transformation or a band pass filter, and fitting said amplitude of respiration induced absorption oscillations with a linear combination of extinction spectra of oxygenated and deoxygenated hemoglobin.

19. A method for measuring a venous oxygen saturation level as in claim 18 wherein said subject being free from mechanical ventilation devices and venous perturbation.

20. A method for measuring the venous oxygen saturation comprising the steps of:
   illuminating an area of tissue with a probe generating intensity modulated light at a plurality of wavelengths;
   sensing diffusely reflected light caused by said illumination to acquire time resolved measurement data;
   processing said time resolved measurement data to determine the absolute saturation of the venous compartment, said processing comprising at least determining an amplitude of respiration induced absorption oscillations; and
   verifying that said measurement data is accurate.

21. A method for measuring the venous oxygen saturation as in claim 20 wherein the step of verifying that said measurement data is accurate comprises measuring time resolved absorption oscillation data at said plurality of wavelengths and verifying that said oscillations are in phase at the respiratory frequency.

22. A method for measuring the venous oxygen saturation as in claim 20 wherein the step of verifying that said measurement data is accurate comprises verifying that said probe is located directly over a visible vein.

23. A method for measuring the venous oxygen saturation as in claim 20 wherein the step of verifying that said measurement data is accurate comprises determining amplitudes of oxygenated and deoxygenated hemoglobin concentration oscillations at a heartbeat frequency and at a respiratory frequency, and verifying that said amplitudes at said heartbeat frequency are less than said amplitudes at said respiratory frequency.

24. A method for measuring the venous oxygen saturation as in claim 20 wherein the step of processing said time resolved data comprises determining absorption data, and wherein the step of verifying that said measurement data is accurate comprises verifying that a hemoglobin spectrum closely agrees with said absorption data.

25. A computer program product for causing a computer to measure the venous oxygen saturation, the program product comprising computer executable instructions stored on a computer readable medium, the program instructions when executed causing the computer to:
   illuminate an area of tissue using a probe generating intensity modulated light at a plurality of wavelengths;
   sense diffusely reflected light caused by said illumination to acquire time resolved measurement data;
   process said time resolved measurement data to determine the absolute saturation of the venous compartment, said processing comprising at least determining an amplitude of respiration induced absorption oscillations; and
   verify that said time resolved measurement data represents venous compartment data.

26. A computer program product as in claim 25, wherein the program instructions when executed cause the computer to verify that said probe is properly located by causing the computer to perform one or more of the steps from the group of steps consisting of: measuring time resolved absorption oscillation data at said plurality of wavelengths and verifying that said oscillations are in phase at the respiratory frequency, and determining amplitudes of oxygenated and deoxygenated hemoglobin concentration oscillations at a heartbeat frequency and at a respiratory frequency and verifying that said amplitudes at said heartbeat frequency are less than said amplitudes at said respiratory frequency.

27. A computer program product as in claim 25 said program instructions being operable when said subject is free from mechanical ventilation devices and venous perturbation.

* * * * *